United States Patent [19]
Stonnet et al.

[11] Patent Number: 5,998,138
[45] Date of Patent: Dec. 7, 1999

[54] NUCLEOTIDE SEQUENCE HYBRIDIZING SPECIFICALLY WITH A GENOMIC NUCLEIC SEQUENCE OF CAMPYLOBACTER

[75] Inventors: Véronique Stonnet, Asnieres; Jean-Luc Guesdon, Sèvres, both of France

[73] Assignee: Institut Pasteur, Paris Cedex, France

[21] Appl. No.: 08/836,197

[22] PCT Filed: Nov. 13, 1995

[86] PCT No.: PCT/FR95/01491

§ 371 Date: Jul. 1, 1997

§ 102(e) Date: Jul. 1, 1997

[87] PCT Pub. No.: WO96/15261

PCT Pub. Date: May 23, 1996

[30] Foreign Application Priority Data

Nov. 14, 1994 [FR] France .................................. 94 13622

[51] Int. Cl.[6] .............................. C12Q 1/68; C12P 19/34; C07H 21/02; C07H 21/04
[52] U.S. Cl. .................................. 435/6; 435/6; 435/91.1; 435/91.2; 435/91.5; 536/23.1; 536/24.3; 536/24.32; 536/24.33
[58] Field of Search .............................. 435/6, 91.1, 91.2, 435/91.5; 536/23.1, 24.3, 24.32, 24.33

[56] References Cited

U.S. PATENT DOCUMENTS 5,654,416  8/1997  Cummins .............................. 536/24.3

FOREIGN PATENT DOCUMENTS 0 232 085     8/1987   European Pat. Off. .
0 350 392 A2  1/1990   European Pat. Off. .

OTHER PUBLICATIONS

Chevrier et al, "Identification and Classification of Campylobacter Strains by Using Nonradioactive DNA Probes," Journal of Clinical Microbiology, pp. 321–326, (Feb. 1989).

Eyers et al, "Discrimination Among Thermophilic Campylobacter Species by Polymerase Chain Reaction Amplification", Journal of Clinical Microbiology, pp. 3340–3343 (Dec. 1993).

Gourse, R.L. et al. Site–directed mutagenesis of ribosomal RNA. J. Mol. Biol. 159:397–416, 1982.

Primary Examiner—Carla J. Myers
Assistant Examiner—Diana Johannsen
Attorney, Agent, or Firm—Oblon, Spivak, McClelland, Maier & Neustadt, P.C.

[57] ABSTRACT

The present invention relates to a nucleic acid sequence isolated from C. coli which hybridizes specifically with the genomic nucleic acid of strains belonging to the species C. coli and which does not hybridize under the usual conditions with the nucleic acids of campylobacteria which do not belong to this species, nor with the genomic nucleic acids of bacteria related to the genus Campylobacter.

16 Claims, 1 Drawing Sheet

SEQUENCE LISTING

<160> NUMBER OF SEQ ID NOS: 3

<210> SEQ ID NO 1
<211> LENGTH: 604
<212> TYPE: DNA
<213> ORGANISM: Campylobacter coli

<400> SEQUENCE: 1

```
ttaaaaagac ttatttccat actaaatcaa cccaaataaa aataaaaaat attatactta      60
aatatccatt taaagtaaaa aacgctttat caatgtgagc aaaattttta tgtacaattt     120
tatgttcaaa agccaaaata ataccgctga taatcattcc aaataatgca atatttccaa     180
gcgctactcc ccaaacctgc caaacaaaaa gtagccaaaa taatactgct aatacatggc     240
aaaagccgag ataaataaag tcgccttaga gccaaattta gcagggatag aatgaagtcc     300 tacttttta tcatactcca tatcttgtaa agagtaaagc aaatcaaatc cagccgtcca     360
```

```
aaaagttacc cctaagcata aaatcacact ataaatgtga atttcaccat gactatcaca      420
ctgcctgcaa taggtgcaag tcctaaacaa aatcctaaaa ctaaatgcgc taaagactaa      480
agcgtttaaa agcagaataa attgccaata caaaaaagca caggaaaaga aagataaaaa      540
gccaaagtat tgataaaata agaacacaat ataaaaataa tcgcattagg ataataaaat      600
ccaa                                                                  604

<210> SEQ ID NO 2
<211> LENGTH: 22
<212> TYPE: DNA
<213> ORGANISM: Campylobacter coli

<400> SEQUENCE: 2
atatttccaa gcgctactcc cc                                               22

<210> SEQ ID NO 3
<211> LENGTH: 22
<212> TYPE: DNA
<213> ORGANISM: Campylobacter coli

<400> SEQUENCE: 3
caggcagtgt gatagtcatg gg                                               22
```

NUCLEOTIDE SEQUENCE HYBRIDIZING SPECIFICALLY WITH A GENOMIC NUCLEIC SEQUENCE OF CAMPYLOBACTER

BACKGROUND OF THE INVENTION

1. Field of the Invention

The present invention relates to a specific nucleic sequence of *Campylobacter coli*, as well as to applications of this sequence as specific nucleotide probe for the detection of sequences of *Campylobacter coli* or of fragments of this sequence as nucleotide primers for the amplification of DNA or RNA of *Campylobacter coli* in a biological specimen.

2. Description of the Background Art

Campylobacter infections are very common all over the world, affecting man as well as wild or domestic animals.

Although discovered at the start of the twentieth century, the bacteria now called Campylobacter were unrecognized for a long time, because their characteristics rendered their identification and their culture difficult. First isolated in sheep and cattle and called *Vibrio fetus* and then, later, *Campylobacter fetus*, it was not until the start of 1946 that the first cases of human campylobacterioses were described, but it was not until the start of 1972, when selective media for Campylobacter had begun to be perfected, that the importance of Campylobacter infections had been able to be proved and recognized.

Since the naming of the species type *Campylobacter fetus*, about a dozen other species and subspecies have been discovered, the exact number varying according to the authors and the taxonomic methods, which often propose novel classification criteria. Among these species, the most frequently encountered in human and/or animal pathology are *Campylobacter jejuni, Campylobacter coli* and *Campylobacter fetus*.

At present, *Campylobacter jejuni* and *Campylobacter coli* are frequently responsible for infectious diarrhoea in man.

The "national surveillance system of Campylobacter infections", set up in France in 1986, publishes each year an assessment making evident the principal epidemiological and clinical data of the cases reported.

In the human species, the major symptom of intestinal infection with *C. jejuni* or with *C. coli* is diarrhoea which, in the most serious cases, can involve serious losses of water, which can be particularly dangerous for children and infants, who are very sensitive to dehydration. However, Campylobacter enteritis is often without complications and diarrhoeas can even cease spontaneously at the end of one week. However, the coprocultures can remain positive up to several weeks or even months, and, in 5 to 10% of the cases, relapses can occur. Treatment and rigorous follow-up are then essential, especially for subjects who are immunodepressed or have serious disorders (AIDS, cirrhosis of the liver, cancer, leukaemia, etc.), in which Campylobacter can behave like opportunistic bacteria.

Other consequences of *C. jejune* or *C. coli* infections have also been described, although rarer or more exceptional: mesenteric adenitis, cholecystitis, urinary infections, meningites, septicaemias, erythema nodosum or Guillain-Barré syndrome, etc.

In animals, the Campylobacter usually live in commensals in the alimentary canal of numerous species: cattle, sheep, pigs, poultry, wild birds, dogs and cats. These animals, whether ill or healthy carriers, form a large reservoir of germs, and thus an important risk of contamination. In the case of obvious infections, in cattle and sheep, *C. jejuni* is known, since the first description in 1931, as being the cause of "bovine dysentery", which can have the result, apart from the effect on the cattle, of transmission to man through the dissemination of germs in the environment of the animals (ground, water). Even for the asymptomatic animals, "healthy carriers", transmission to man can take place: either by direct contact with these animals or their excrement, or by consumption of contaminated food or water (meats contaminated during their preparation and badly cooked, non-pasteurized milk, polluted water, etc.).

From a prevention viewpoint, it is important then, both in man and in animals, to be able to identify the pathogen *C. jejuni* or *C. coli* as soon as possible, in order to prevent, by means of adequate measures, any contamination. This is particularly the case in the farm-produce industry, where conditions of sterility must be respected. It is equally important in human pathology, to carry out a proper follow-up of the disorders treated following a Campylobacter infection, in order to avoid any new relapse.

Finally, in the case of notified infections, it is very important to identify properly the germ responsible, and to do this rapidly after the triggering of the disorder, in order to be able to administer a proper and efficacious treatment which will prevent the progress of the infection, or even the growth of epidemics. However, the identification of the Campylobacter and the determination of the incriminated species is not easy. In fact, their isolation requires special media and their conventional detection does not take place at present until after an enrichment by culturing for at least 48 hours. This is very long when a rapid diagnosis is necessary. On the other hand, given that the microbiological diagnosis takes place at present by bacteriological and/or biochemical techniques which exploit phenotype differences existing between the different species, errors of diagnosis can occur, especially when mutants appear for a given characteristic. In the distinct case of *C. jejuni* and *C. coli*, the unique criterion of differentiation is hydrolysis of hippurate (*C. jejuni* can hydrolyse it although *C. coli* cannot), and it sometimes happens that this distinction cannot be made because there are hippurate-negative *C. jejuni* strains (Hébert et al., J. Clin. Microbiol., 1984, 20, 138–104, Totten et al., J. Clin. Microbiol., 1987, 25, 1747–1752).

Approaches using molecular hybridization to identify the strains belonging to the genus Campylobacter have been proposed. However, these methods do not allow identification until after culture; they are not sufficiently sensitive to detect this bacterium in the biological samples. Thus, methods of identification and of classification of Campylobacter have been proposed using either radioactive probes (Ng et al., Mol. Cell. Probes, 1987, 1, 233–243), or non-radioactive probes (Chevrier et al., J. Clin. Microbiol., 1989, 27, 321–326), but these methods use total genomic probes and necessitate enrichment by culture of the pathogen to be detected, because the threshold of detection is sufficiently high, approximately $10^5$ bacteria (Chevrier et al., above).

Research on specific nucleic probes of *C. jejuni*, with an aim of diagnosis of species, has been performed by Picken et al., (Mol. Cell. Probes, 1987, 1, 245–259), Korolik et al., (J. Gen. Microbiol., 1988, 134, 521–529) and Zhou and Wang (Zbl. Bakt., 1989, 272, 186–190), but there remain problems of specificity and the sequences of these potential probes have not been determined.

Recently the inventors, the authors of the present invention, have discovered a specific DNA sequence of the species *C. jejuni* (FR-2 701 028). This sequence has been used to perfect a PCR test capable of detecting and identifying this species in a biological specimen (Stonnet and Guesdon, FEMS Immunol. Med. Microbiol., 1993, 7, 337–344). Taking account of the high specificity of the sequence, this PCR test does not allow the species *C. coli*, which is just as important clinically as *C. jejuni* to be detected. Recently, a specific method of identification of and of discrimination among the thermophilic Campylobacter, including *C. coli*, has been described by Eyers et al., (J. Clin. Microbiol., 1993, 31, 3340–3343). However, the specific primers of species have been chosen in hypervariable regions of the genes coding for 23S ribosomal RNA, which does not exclude the possibility of obtaining "false-negative" results when the DNA of a strain to be tested possesses variations just at the sequence of the primers.

SUMMARY OF THE INVENTION

However, these reasons have led the inventors to choose as an objective to isolate specific DNA sequences of *Campylobacter coli* and to develop starting from these sequences a method of identification based on the PCR technique and the technique of molecular hybridization. The combination of these two techniques allows a very low detection threshold to be attained, allowing a single *C. coli* bacterium to be detected and identified in a biological specimen.

The inventors have now isolated a nucleic sequence utilizable for the specific detection of the species *Campylobacter coli*.

The present invention thus relates to a nucleotide sequence which hybridizes specifically with the genomic nucleic acid of the strains belonging to the species *C. coli* and which does not hybridize under the usual conditions with the nucleic acids of campylobacteria not belonging to this species, or with the genomic nucleic acids of bacteria related to the genus Campylobacter.

The invention likewise relates to a nucleic acid sequence having the sequence SEQ ID No. 1, the complementary sequence to this, or a sequence which differs from it by mutation, insertion, deletion or substitution of one or more bases.

DETAILED DESCRIPTION OF THE INVENTION

"Sequence which differs from it by mutation, insertion, deletion or substitution by one or more bases" is understood as meaning a sequence which hybridizes with the sequence SEQ ID No. 1 or its complementary sequence under the usual conditions of stringency defined by Sambrook J., Fritsch E. F. and Maniatis T. (1989): Molecular Cloning: A Laboratory Manual, Ed. Cold. Spring Harbor Laboratory (9.47–9.62).

These conditions are determined from the mean melting temperature $T_m$.

Preferably, the most advantageous sequences are those which hybridize in the temperature range ($T_m$–15° C.) to ($T_m$–20° C.).

The sequences in question advantageously comprise at least 12 nucleotides.

The invention likewise relates to a cloning vector containing a nucleotide sequence such as defined above, more particularly the plasmid pCS1 containing the sequence SEQ ID No. 1 deposited under the Budapest Treaty on Nov. 14, 1994 at the Collection National de Cultures de Microorganismes, Institut Pasteur, 28, Rue du Docteur Roux, F-75724 PARIS CEDEX 15, under accession no. I-1491.

The nucleotide sequences defined above can be DNA sequences or RNA sequences.

The exact size of the fragment of sequence SEQ ID No. 1 is 604 bp.

At first, the fragment CS1 was used in a hybridization test, following the technique of Southern, on genomic DNAs of different strains of the species *C. coli* (*C. coli* CIP 70.54, *C. coli* CIP 70.77, *C. coli* CIP 70.78, *C. coli* CIP 70.79, *C. coli* CIP 70.80, *C. coli* CIP 70.81, *C. coli* CIP 71.5, *C. coli* CIP 103753, *C. coli* A630 clinical isolate) digested by the enzyme HindIII, BglII and EcoRV, respectively. All the strains possess DNA fragments which hybridize with the probe CS1. According to the enzyme used, HindIII, BglII and EcoRV, these fragments have a size of 2.3 kb, 3.5 kb or 2.7 and 6 kb, respectively.

In another test of the same type, the CS1 fragment was used as a probe on target DNAs from other species of Campylobacter (*Campylobacter jejuni, C. lari, C. fetus* subsp. *fetus, C. fetus* subsp. *venerealis, C. hypointestinalis, C. sputorum* subsp. *sputorum, C. sputorum* subsp. *bubulus, C. concisus, C. curvus* and *C. fecalis*) or other bacterial genera (*Escherichia coli, Arcobacter cryaerophylus, Helicobacter pylori, Salmonella typhimurium*). These target DNAs were digested by the enzyme HindIII. A significant hybridization with the DNA of *C. coli* (positive control) was observed, 3 h after autoradiography. After exposure for 24 hours, a slight signal is visible from the DNA of *C. jejuni*. This slight cross-hybridization is not inexplicable, because there is 30 to 50% homology at the genomic level between *C. jejuni* and *C. coli*. The CS1 fragment is not hybridized with any of the other DNAs tested. No signal was visible on autoradiography, even after very long exposure times (72 hours).

The sequence SEQ ID No. 1 of the parts or of functionally equivalent variants of these can be used in molecular hybridization techniques for the detection and identification of *Campylobacter coli*.

The functionally equivalent variants include sequences in which base pairs have been mutated, deleted, inserted or substituted without the essential properties regarding the specificity of these fragments being affected.

The nucleotide sequences according to the invention have diagnostic and epidemiological applications in human or veterinary medicine, especially as specific nucleic probes for *Campylobacter coli* or as oligonucleotide primers for the amplification of a specific sequence of *Campylobacter coli*.

The probes according to the invention advantageously comprise at least 20 consecutive nucleotides among the sequences or the fragments of sequences mentioned above.

The probes are DNA probes or RNA probes.

The nucleotide sequences described in this invention can thus be used as probes to detect specifically and in a direct manner strains of *Campylobacter coli* in a biological specimen. The unlabelled sequences can be used directly as probes, however the sequences are generally labelled by a radioactive element ($^{32}P$ $^{35}S$, $^{3}H$, $^{125}I$) or by a non-radioactive molecule (biotin, acetylaminofluorene, digoxigenin, 5-bromodeoxyuridine) to obtain probes utilizable for numerous applications.

In this last case, it would be possible to use one of the labelling methods described in FR 2 422 956 and FR 2 518 755. The hybridization technique can be carried out in various manners (Matthews, J. A. and Kricka, L. J., Anal. Biochem. 1988, 169, 1–25). The most general method consists in immobilizing the nucleic acid extracted from cells of *Campylobacter coli* on a support (nitrocellulose, nylon, polystyrene, . . . ) and in incubating, under well-defined conditions, the target nucleic acid immobilized with the probe. After hybridization, the excess of probe is eliminated and the hybrid molecules formed are detected by the appropriate method (measurement of the radioactivity, of the fluorescence or of the enzymatic activity connected with the probe . . . ).

In another application, the nucleic acid probes described here can be used as capture probes. In this process, the probe is immobilized on a support and serves to capture by specific hybridization the target nucleic acid extracted from *C. coli*. If necessary, the solid support is separated from the specimen and the duplex formed between the capture probe and the target nucleic acid is then detected by means of a second detection probe labelled with an easily detectable element.

When a sufficient quantity of nucleic acid of *Campylobacter coli* can be extracted from samples to be analysed, the sequences described in the patent are utilizable for detecting and identifying the strains belonging to *Campylobacter coli* directly in these samples. In the opposite case, rapid culture in liquid medium can be carried out before the extraction of the nucleic acid of *Campylobacter coli*, or else the small quantity of nucleic acid of *Campylobacter coli* extracted from the sample can be subjected to an amplification technique such as the PCR technique.

The sequence SEQ ID No. 1 and its derived sequences can likewise be used to select oligonucleotide primers, especially for the PCR technique.

This technique necessitates the choice of pairs of oligonucleotides surrounding the fragment which is to be amplified (U.S. Pat. No. 4,683,202). These oligodeoxyribonucleotide or oligoribonucleotide primers advantageously have a length of between 18 and 30 and, preferably, 18 to 22 nucleotides. One of the two primers is complementary to the (+) strand of the matrix and the other primer is complementary to the (−) strand. It is important that these primers do not possess a secondary structure or a complementary sequence one to the other. Moreover, the length and the sequence of each primer must be chosen in such a manner that the primers to not hybridize with other nucleic acids from prokaryotic or eukaryotic cells, in particular with the nucleic acids of Campylobacter not belonging to the species coli and with human DNA or RNA which may possibly contaminate the sample.

The amplimers selected as specific primers for the amplification of nucleic sequences of strains belonging to *Campylobacter coli* are chosen, for example, following the method described by Griffais et al., (Nucleic Acids Res. 1991, 19, 3887–3891).

Starting from the sequence SEQ ID No. 1, the inventors chose oligonucleotides to carry out a PCR test. By means of these oligonucleotides they obtained a specific amplification of *Campylobacter coli*, no amplification being visible with the DNA of the 10 other Campylobacter mentioned above, in particular *C. jejuni*, or with the DNA of *Escherichia coli, Helicobacter pylory, Salmonella typhimurium* and *Arcobacter cryaerophilus*.

A pair of very particularly preferred primers is represented by the oligonucleotides CSF and CSR originating from the sequence SEQ ID No. 1, of sequences:

CSF primer: 5'ATA TTT CCA AGC GCT ACT CCC C3'
SEQ ID NO:2
CSR primer: 5'CAG GCA GTG TGA TAG TCA TGG G3'
SEQ ID NO:3

The fragments of nucleic acid obtained by genetic amplification with the aid of the primers described above likewise form a subject of the invention.

The amplified fragments can be identified after electrophoresis on agarose or polyacrylamide gel, or after capillary electrophoresis, or alternatively after a chromatography technique (gel filtration, or hydrophobic or ion-exchange chromatography). The specificity of the amplification can be controlled by molecular hybridization using as a probe the nucleotide sequence SEQ ID No. 1, fragments of this, plasmids containing these sequences or fragments of these, complementary oligonucleotides of these sequences or fragments of sequences or of amplification products. These probes may or may not be labelled by radioactive elements or by non-radioactive molecules.

The present invention likewise relates to a method of detection of the presence of strains of *Campylobacter coli* in a biological specimen, characterized by the following steps:

i) contacting of the biological specimen with a pair of oligonucleotide fragments called primers, such as defined above, the nucleic acid contained in the specimen having, if necessary, been previously rendered accessible to hybridization and under conditions allowing hybridization of the primers with the nucleic acid of the strains belonging to *Campylobacter coli;* ii) amplification of the nucleic acid of the strains of *Campylobacter coli;* iii) demonstration of the amplification of fragments of nucleic acid corresponding to the fragment surrounded by the primers;

iv) possible verification of the sequence of the amplified fragment, for example by specific probe hybridization, by sequencing or by restriction site analysis.

The present invention in addition relates to a kit or pack for the detection of the presence of strains belonging to *Campylobacter coli* in a biological specimen, characterized in that it comprises the following elements:

a pair of oligonucleotide fragments such as defined above;

the reagents necessary for carrying out an amplification of nucleic acid of strains belonging to *Campylobacter coli;* if possible, a component allowing the sequence of the amplified fragment to be verified, more particularly a nucleic probe such as defined above.

This kit more advantageously contains the labelled or unlabelled probe(s). These can be in solution or immobilized on a support. The kit can likewise contain the reagents necessary for the lysis of the bacteria and the extraction of the target nucleic acids, as well as the hybridization and washing solutions corresponding to the chosen method.

BRIEF DESCRIPTION OF THE DRAWINGS

The invention is illustrated in more detail in the examples which follow and the annexed figures, in which.

EXAMPLE 1

Figure 1:
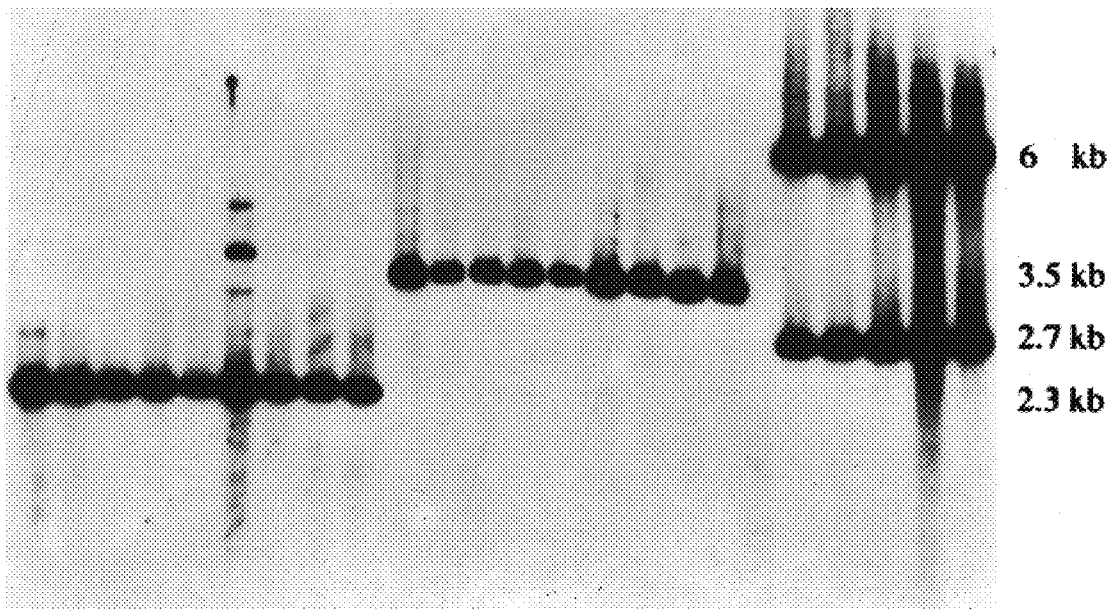
FIG. 1 represents the hybridization profiles of the DNAs of different strains of *C. coli* with the CS1 fragment used as a probe.
Figure 2:
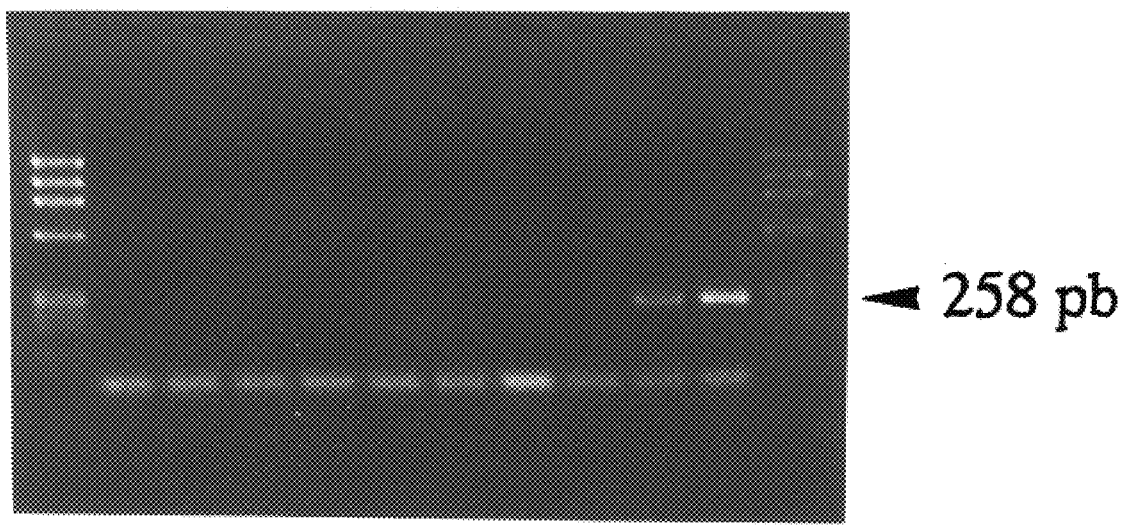
FIG. 2 represents the electrophoresis results obtained after amplification by PCR with the CSF and CSR pair of primers.

Construction of the geneomic bank of *C. coli*. Screening of the bank and determination of the sequence of the specific fragment:

The genomic DNA of *C. coli* CIP 70.80 is partially digested by the restriction endonuclease HindIII by acting 0.5 U of enzyme per µg of DNA in the buffer recommended by the manufacturer for 1 hour at 37° C. These conditions allow the preferential obtainment of fragments of length of between 30 and 40 kb. After digestion, the mixture containing the DNA fragments is purified by phenol/chloroform extractions and the DNA is precipitated with ethanol.

The vector is the cosmid pHC79. It is digested by the enzyme HindIII and dephosphorylated to avoid any autoligation.

The ligation is carried out by mixing 700 ng of vector and 3 μg of DNA fragments of 30/40 kb, and the mixture is left at 12° C. for 18 hours after having added 5 units of T4 DNA ligase in an appropriate buffer.

The recombinant cosmids are encapsidated in vitro and used to transform the bacteria (E. coli HB 101). The transformed bacteria are incubated for 1 hour at 37° C. in LB medium, then spread onto selective agar media containing 25 μg/ml of ampicillin. The colonies resistant to ampicillin are then all tested for their sensitivity to tetracycline; in fact the DNA fragment of 30/40 kb is inserted into the vector so as to inactivate the resistance gene to tetracycline (Tet) and to preserve the resistance gene to ampicillin (Amp).

A mini preparation of DNA of 200 first transformant colonies resistant to ampicillin (Amp$^r$) and sensitive to tetracycline (Tet$^s$) is carried out according to the alkaline lysis technique. The DNA of these preparations is then digested by the restriction endonuclease HindIII, analysed by electrophoresis on 0.8% agarose gel, and then transferred to nylon filters. The DNA is irreversibly fixed by exposure to UV at 254 nm for 3 minutes.

These different filters are incubated for 16–18 hours at 65° C. in a 6× SSC buffer (1× SSC corresponds to 0.15M NaCl and 0.015M Na citrate) containing 10% dextran sulphate, a solution of concentrated Denhardt 5× (a solution of Denhardt 1× corresponds to 0.02% of Ficoll, 0.02% of polyvinylpyrrolidone and 0.02% of bovine serum albumin), 10 mM EDTA, 0.5% SDS, 100 μg/ml of denatured salmon sperm DNA and the genomic DNA, radiolabelled with $^{32}$P by multipriming, of one of the two following species: C. jejuni CIP 70.2, C. coli CIP 70.80.

After hybridization, the filters are washed twice for 10 minutes in 2× SSC at 65° C., once for 30 minutes in 2× SSC+0.1% SDS at 65° C., and finally once for 10 minutes in 0.1× SSC at 65° C. The filters which are still damp are subjected to autoradiography at –80° C. with an intensifying screen for from 15 minutes to 3 days.

The results of these hybridizations allowed a cosmid clone containing a fragment of approximately 2.3 kb, called CS1, to be isolated.

The specificity of the fragment was verified as described in Example No. 2.

The CS1 fragment was sequenced according to the Sanger method using the T7 sequencing kit (Pharmacia) directly on the cosmid, after alkaline denaturation of the two strands of DNA. All the sequencing reactions were carried out with dATP labelled with $^{35}$S.

The sequenced part (600 base pairs) of the fragment is represented in the listing attached to the description. The comparison between the "Genebank" and "EMBL" databanks and the 600 nucleotides of the fragment CS1 thus determined does not cause any significant homology to emerge with the sequences known today.

EXAMPLE 2

Analysis of DNA by the Southern technique, using as probes the nucleic acid sequences of the invention:

The list and the references of the bacteria used in this study are the following:

Campylobacter:
C. jejuni subsp. jejuni CIP 70.2, CIP 70.86, CIP 81.1
C. jejuni subsp. doylei CIP 103751
C. coli CIP 70.80, CIP 71.5, CIP 70.81, CIP 70.79, CIP 70.78, CIPI 70.77, CIP 70.54
C. lari CIP 102722
C. upsaliensis CIP 103681
C. fetus subsp. fetus CIP 5395
C. fetus subsp. venerealis CIP 6829
C. hyointestinalis (clinical isolate)
C. sputorum subsp. sputorum CCUG 9728
C. sputorum subsp. bubulus CIP 53103
C. concisus (clinical isolate)
C. fecalis CIP 12014
C. Curvus (clinical isolate)
Non-Campylobacter:
Arcobacter cryaerophila CCUG 17801
Helicobacter pylori CIP 101260
Escherichia coli HB101
Salmonella subsp. typhimurium C 53
Salmonella subsp. salamae
Salmonella subsp. diarizonae
Enterococcus fecalis JH2-SM
Enterococcus faeclum D372 (clinical isolate)
Bacteroides fragilis E134 (clinical isolate)
Bacteroides fragilis F238 (clinical isolate)

The results are represented in FIG. 1, the number of the tracks corresponding in order to the strains listed above.

DNA of bacteria belonging to the genus
Campylobacter, other than C. coli

After culture in appropriate medium (5% sheep blood agar, Biomérieux), the Campylobacter are treated in the following manner: the bacteria of each Petri dish are harvested with 2 ml of TE-glucose buffer (25 mM tris HCl, pH 8, 10 mM EDTA, 50 mM glucose) and centrifuged for 5 minutes at 5000 g, the pellet is redispersed and washed in TE-glucose and then recentrifuged, the bacteria are resuspended in 100 μl of TE buffer (10 mM tris HCl, pH 8, 1 mM EDTA) and the DNA is extracted according to the technique of Pitcher et al., (Lett. Appl. Microbiol., 1989, 8, 151–156). Two μg of the DNA thus extracted are subjected to a total digestion by the enzyme HindIII. The fragments obtained are then separated by electrophoresis on agarose gel containing 0.8% of TAE before being transferred to nylon membrane according to the Southern technique.

The fragments transferred are analysed by molecular hybridization. The probe CS1, labelled by $^{32}$P, specifically detects the DNA of C. coli and does not hybridize with the genomic DNA of other Campylobacter, except very slightly with a DNA fragment situated on the genome of C. jejuni. This cross-hybridization is not detectable until after 18 hours of exposure, whereas the DNA of C. coli is detectable after 3 hours of exposure.

DNA of bacteria not belonging to the genus
Campylobacter

The DNA of these bacteria and of C. coli used as positive control was hydrolysed by the restriction enzyme HindIII, and then the fragments were separated by electrophoresis on agarose gel and transferred onto a Hybond-N nylon membrane. These different DNA fragments are analysed by molecular hybridization, using as a probe the fragment CS1 labelled with $^{32}$P according to the technique of the random primed DNA labelling kit (Boehringer). Autoradiography shows that the only species detected is C. coli. No hybridization is detectable on the DNA of the non-campylobacteria species, even after 72 hours exposure.

EXAMPLE 3

In vitro enzymatic amplification of the DNA of C. coli with the primers defined starting with the nucleic acid sequence to which the invention relates.

Choice of Primers

It has been shown that it is essentially the 3' end of the oligonucleotide primers which determines the specificity of the PCR. It is thus important that this 3' region be perfectly specific to the target to be amplified.

Given that the genome of Campylobacter has a very low percentage of guanine and cytosine (between 28 and 38% of G+C), the inventors thought that primers whose 3' end was rich in G+C could have a high degree of specificity.

With the aid of a computer program the inventors found, inside the sequence CS1, zones rich in G+C which are present only once on CS1. It is starting from these regions that the sequence of the primers has been positioned and completed so as to obtain a length of about twenty nucleotides.

Synthesis of the Oligonucleotide Primers

The primers derived from the sequence CS1, called CSF and CSR and having a length of 22 nucleotides, were synthesized with the aid of a phosphoramidite method on an automatic system by the organic chemistry service of the Institut Pasteur. The concentration of each primer is determined on the spectrophotometer.

Amplification

The in vitro enzymatic amplification technique (PCR) is carried out according to the protocol described by Saiki et al. (Science, 1988, 239, 487–491) using 1 $\mu$M CSF and CSR oligonucleotides and 30–100 ng of DNA of different strains of Campylobacter with 0.5 units of Taq polymerase in a buffer containing 25 mM KCl, 20 mM tris HCl, pH 8.5, 1.5 mM $MgCl_2$, 200 $\mu$M deoxyribonucleotide trisphosphates and 100 $\mu$g/ml of bovine serum albumin, the final volume of the reaction being 50 $\mu$l. The parameters of the PCR stages were chosen in the following fashion: 5 minutes at 94° C., 1 minute at 60° C., 1 minute at 72° C., then (1 minute at 94° C., 1 minute at 60° C., 1 minute at 72° C.) 38 times and a last cycle of 1 minute at 94° C., 1 minute at 60° C. and 5 minutes at 72° C. Forty cycles are then carried out using an automatic apparatus. After the last cycle, the specimens are kept at 4° C. until analysis.

Electrophoretic analysis on agarose gel of the amplified specimens

Ten $\mu$l of the amplified specimens are deposited on a 2% agarose gel in a TBE buffer (0.04 M tris-borate, 0.001 M EDTA) containing 1 $\mu$g/ml of ethidium bromide. The amplified fragments are visualized under UV and the gels are photographed using a Polaroid 667 film.

The results obtained with DNAs of different species of Campylobacter and the CSF and CSR primers show that the length of the amplified fragment obtained corresponds to the theoretical length expected with this pair of primers and which is 258 base pairs.

Further to these results, any fragment amplified is not visible when the DNA analysed is an extract of the following species or genera: C. jejuni subsp. jejuni, C. jejuni subsp. doylei, C. lari, C. upsaliensis, C. fetus subsp. fetus C. fetus subsp. venerealis, C. hyointestinalis, C. cryaerophila, C. sputorum subsp. sputorum, C. sputorum subsp. bubulus, C. fecalis, C. concisus, C. curvus, Escherichia coli, Helicobacter pylory, Arcobacter cryaerophilus, Salmonella subsp. salamae, Salmonella subsp. diarizonae, Enterococus fecalis, Enterococcus faecium, Bacteroides fragilis or of human cells. Of course, all the strains of C. coli tested gave positive results, be they collection strains or isolates from sick people.

In conclusion, all these results demonstrate that, with the aid of the PCR technique and of primers described in this invention, it is possible specifically to detect the species C. coli, which leads one to think that isolates of sick people and biological specimens infected by C. coli could be identified, thus rendering the method utilizable in the field of clinical bacteriology, in veterinary meedicine and in the farm-produce industry.

---

We claim:

1. A nucleic acid sequence that specifically hybridizes with a genomic nucleic acid of *Campylobacter coli*, said nucleic acid sequence selected from the group consisting of:
   a) SEQ ID NO: 1;
   b) the complement of SEQ ID NO: 1; and
   c) a nucleotide sequence differing from SEQ ID NO: 1 by mutation, insertion, deletion or substitution of one or more bases, wherein said nucleotide sequence hybridizes to SEQ ID NO: 1 or the complement of SEQ ID NO: 1 under high stringency conditions.

2. A vector containing the nucleic acid sequence according to claim 1.

3. A nucleic acid probe that specifically hybridizes with a genomic nucleic acid of *Campylobacter coli*, said probe comprising at least 20 consecutive nucleotides of the nucleic acid sequence of claim 1.

4. A nucleic acid probe according to claim 3, which is a capture probe immobilized on a solid support.

5. An oligonucleotide primer that specifically hybridizes with a genomic nucleic acid of *Campylobacter coli*, said primer comprising 18 to 30 consecutive nucleotides of the nucleic acid sequence of claim 1.

6. A primer pair consisting of two oligonucleotide primers according to claim 5.

7. A primer pair consisting of SEQ ID NO:2 and SEQ ID NO:3.

8. A nucleic acid fragment obtained by amplifying *C. coli* nucleic acids with the primer pair of claim 6.

9. A nucleic acid fragment obtained by amplifying *C. coli* nucleic acids with the primer pair of claim 7.

10. A method for detecting *C. coli* in a biological specimen, comprising:
    a) amplifying nucleic acids from a biological specimen with the primer pair of claim 6; and
    b) detecting a nucleic acid product produced by said amplification as indicative of the presence of *C. coli*.

11. The method of claim 10, further comprising verifying the identity of the nucleic acid product by hybridization, sequencing, or restriction enzyme site analysis.

12. A kit for detecting *C. coli* in a biological specimen, said kit comprising:
    a) a primer pair according to claim 6;
    b) reagents for amplification of nucleic acids; and
    c) optionally, reagents for verifying the identity of a nucleic acid product obtained by amplification with said primer pair.

13. A method for detecting *C. coli* in a biological specimen, said method comprising:
    a) amplifying nucleic acids from a biological specimen with the primer pair of claim 7; and
    b) detecting a nucleic acid product produced by said amplification as indicative of the presence of *C. coli*.

14. The method of claim 13, further comprising verifying the identity of the nucleic acid product by hybridization, sequencing, or restriction enzyme site analysis.

15. A kit for detecting *C. coli* in a biological specimen, said kit comprising:
    a) a primer pair according to claim 7;
    b) reagents for amplification of nucleic acids; and
    c) optionally, reagents for verifying the identity of a nucleic acid product obtained by amplification with said primer pair.

16. The recombinant plasmid pCS1 present in cells having CNCM accession no. I-1491.

* * * * *

UNITED STATES PATENT AND TRADEMARK OFFICE
CERTIFICATE OF CORRECTION

PATENT NO. : 5,998,138

DATED : December 7, 1999

INVENTOR(S): Veronique STONNET et al.

It is certified that an error appears in the above-identified patent and that said Letters Patent is hereby corrected as shown below:

On the title page, item [75], the 1st Inventor's residence is erroneously listed. It should be:

--[75] Inventors: Véronique Stonnet, Malvern, Pennsylvania; Jean-Luc Guesdon, Sèvres, France--

Signed and Sealed this

Twenty-third Day of January, 2001

Attest:

Q. TODD DICKINSON

*Attesting Officer*     *Commissioner of Patents and Trademarks*